United States Patent [19]

Schmitz et al.

[11] Patent Number: 4,564,373
[45] Date of Patent: Jan. 14, 1986

[54] METHOD FOR BUBBLE-FREE GAS FEED

[75] Inventors: Franz J. Schmitz; Rudi Wollbeck, both of Erlenbach; Wolfgang Klein, Klingenberg, all of Fed. Rep. of Germany

[73] Assignee: Akzo N.V., Arnhem, Netherlands

[21] Appl. No.: 357,560

[22] Filed: Mar. 12, 1982

Related U.S. Application Data

[63] Continuation-in-part of Ser. No. 352,846, Feb. 26, 1982, abandoned.

[30] Foreign Application Priority Data

Mar. 2, 1981 [DE] Fed. Rep. of Germany ....... 3107874

[51] Int. Cl.$^4$ .............................................. B01D 53/22
[52] U.S. Cl. ........................................ 55/16; 210/638
[58] Field of Search ............................. 55/16; 210/638

[56] References Cited

U.S. PATENT DOCUMENTS

| | | | |
|---|---|---|---|
| 3,335,545 | 8/1967 | Robb et al. ............................... | 55/16 |
| 3,396,510 | 8/1968 | Ward, III et al. ........................ | 55/16 |
| 3,625,734 | 12/1971 | Ward, III ............................ | 55/16 X |
| 3,733,776 | 5/1973 | Li et al. .................................... | 55/16 |
| 3,770,842 | 11/1973 | Steigelmann et al. ............... | 55/16 X |
| 4,115,514 | 9/1978 | Ward, III ............................ | 55/16 X |
| 4,117,079 | 9/1978 | Bellows ............................... | 55/16 X |
| 4,119,408 | 10/1978 | Matson ................................ | 55/16 X |
| 4,147,754 | 4/1979 | Ward, III ............................ | 55/16 X |
| 4,174,374 | 11/1979 | Matson ................................ | 55/16 X |
| 4,318,714 | 3/1982 | Kimura et al. .......................... | 55/16 |

*Primary Examiner*—Robert Spitzer
*Attorney, Agent, or Firm*—Michael J. Striker

[57] ABSTRACT

A method for the bubble-free feed of gaseous reactants of a chemical and/or biological reaction into a liquid reaction medium, characterized by filling the pores of a porous polymer membrane with the reaction medium, providing one side of the porous polymer membrane with the gaseous reactants, and immersing the other side of the porous polymer membrane into the liquid reaction medium. The pressure of the gaseous reactants should lie below the bubble pressure determined for the reaction medium, but be at least so great that the liquid reaction medium does not pass through the porous polymer membrane to the gas side. Preferred parameters include relative pore volume between 50 and 90%; maximal pore diameter between 0.2 and 3 μm; and disposing the porous polymer membrane in the form of a flat membrane, tube or hollow filaments.

8 Claims, No Drawings

METHOD FOR BUBBLE-FREE GAS FEED

CROSS-REFERENCE TO RELATED APPLICATION

This application is a continuation-in-part application of our copending application Ser. No. 352,846, filed Feb. 26, 1982, now abandoned and entitled A Process for the Bubble-Free Introduction of Gases.

BACKGROUND OF THE INVENTION

The invention concerns a method for the bubble-free feed of gaseous reactants of a chemical and/or biological reaction into a liquid reaction medium.

It is already known from German Offenlegungsschrift DE-OS No. 28 08 293 to feed gas through a membrane into a reaction medium, with the membrane containing a catalyst, which frees the gas from a gas-generating reagent, which then is absorbed by the medium. Such catalytic membranes have previously been used mainly in artificial lungs and in aquariums for oxygen feed, whereby it has been proven directly to be advantageous that a higher oxygen content, which is desired with these uses, be adjusted, and the formation of bubbles upon high oxygen supply effects no disadvantages.

German patent application No. P 30 42 281.2 concerns a method for oxygen concentration, with which the mentioned catalytic membrane is used.

For some chemical and/or biological reactions there exists the necessity of so introducing gaseous reactants that they form no foam with the reaction medium, and with which locally no too high concentrations appear. An example of such a reaction is the growth of cell cultures in a nutrient solution. By reaction medium should be understood liquids, which absorb the gas and in which the other reaction partners are dissolved and/or dispersed.

SUMMARY OF THE INVENTION

It is therefore an object of the present invention to provide a method which allows gaseous reactants to be fed bubble-free, in adjustable amounts, into a reaction medium.

This object is attained according to the present invention through a method which is thereby characterized in that the pores of a porous polymer membrane are filled with the reaction medium, and subsequently one side of the porous polymer membrane is provided with the gaseous reactant, while the other side of the porous polymer membrane is immersed in the liquid reaction medium.

It was extremely surprising and not foreseeable that a filling of the pores in a porous polymer membrane, which is not forced out from the membrane through the provided gas, represents no obstruction for the material passage of the gas into the reaction medium. One can demonstrate that the liquid-filling of the pores represents a diffusion membrane, through which the gas, based upon the concentration gradient, is fed into the reaction medium, which is directed past, along the porous polymer membrane. An increase in pressure on the side of the porous polymer membrane which is provided with the gaseous reactants leads to an increased material passage. The reason for this can be seen in that through the increased pressure the layer thickness of this "liquid diffusion membrane" is decreased.

Preferably, the pressure of the gaseous reactants lies below the bubble pressure determined with the reactants, but is at least so great that the liquid reaction medium does not pass through the porous polymer membrane to the gas side.

With porous polymer membranes, for characterization of the pore size, the bubble point is determined, through which the pressure is given at which air begins to pass through an alcohol-soaked polymer membrane, in the form of bubbles (ASTM-Method F316–70, 1976). The correspondingly determined pressure, whereby the porous polymer membrane is soaked with the reaction medium instead of with alcohol, is preferably the upper limit for the pressure of the gaseous reactants. With the pressure the amount of gas diffusing through the membrane is allowed to increase, whereby the pressure should not come up to the amount at which the liquid reaction medium passes through the porous polymer membrane to the gas side.

As polymer membrane, each known porous polymer membrane can find use which is inert relative to the reaction medium and the gaseous reactants. They can be used as flat membrane, tube or as hollow filaments.

Suitable as porous polymers are for example regenerated cellulose, cellulose ester, e.g. cellulose acetate, polyacrylonitrile, polyamide, polyester and polyolefins, in particular also polypropylene.

Methods for the production of such porous polymer membranes are described for example in German Offlegungsschriften DE-OS No. 27 37 745 and DE-OS No. 28 33 623, as well as in German patent applications Nos. P 30 06 880.5-41, P 30 26 718.6, P 30 42 110.4, as well as P 30 49 557.9.

With the presently determined stipulations with regard to limiting surface characteristics of the porous polymer membranes to the reaction medium, one counters difficulties in filling the pores with the reaction medium. This is the case for example with porous polypropylene membranes. The filling of the pores succeeds, however, without difficulties when the porous polymer membrane is made wettable for the reaction medium, through suitable measures. With many polymers, one succeeds through treatment with swelling agents for the polymer. An expedient method for polypropylene membranes resides in initially soaking the membrane with a liquid having a low surface tension, for example an alcohol, which is miscible with the reaction medium, and subsequently expelling this liquid through rinsing with the reaction medium. If for example the reaction medium is an aqueous nutrient solution, then the expulsion can also follow initially through water, with the water then later being expelled by the reaction medium.

One potentiality for increasing the amount of gaseous reactants to be fed in involves the relative pore volume of the porous polymer membrane. This results from the density of the porous polymer membrane $\gamma_a$ and the density of the pore-free polymer material $\gamma_p$, according to the formula $$V_{pores} = 100 \cdot \left(1 - \frac{\gamma_a}{\gamma_p}\right)$$

Preferably, the relative pore volume amounts to between about 50 and 90%.

Further possibilities for increase other than what has already been mentioned involve the temperature and the surface of the porous polymer membrane. With increasing temperatue, the rate of diffusion increases, but the solubility of a reaction medium for the gaseous reactants decreases, so that a temperature increase can then be of advantage when the reaction consuming the gaseous reactants is accelerated only through the temperature, and the lower solubility is compensated.

The method according to the present invention allows in simple manner for gaseous reactants to be led in strictly dosed amounts into a reaction medium in which a chemical and/or biological reaction occurs. With biological reactions, this allows for example an increase in the growth and propagation of cell cultures. With chemical reactions the supply of gaseous reactants, for different reasons, can be desirable only in definable amounts per unit time, for example since they involve very toxic and/or valuable gaseous reactants. Examples of such reactants, with which one wishes to avoid a corresponding gas atmosphere above the reaction medium, are, for example, hydocyanic acid, phosgene or cyanogen chloride. Particularly important are reactions with which oxygen must be introduced dosed to as great an extent as possible. Appertaining thereto, also with an appropriately great exchange surface, is the use of the method according to the present invention with artificial lungs.

When porous polymer membranes are used, having extremely large pore diameters, the possibilities of increase with respect to the pressure are strongly limited, so that according to the present invention porous polymer membranes are preferred for which the maximal pore diameter amounts to between 0.2 and 3 $\mu$m.

The novel features which are considered characteristic for the invention are set forth in particular in the appended claims. The invention itself, however, both as to its construction and its method of operation, together with additional objects and advantages thereof, will be best understood from the following description of specific embodiments.

DESCRIPTION OF THE PREFERRED EMBODIMENTS

Example 1

An important area of use for the method according to the present invention is the bubble-free supplying of oxygen into an aqueous nutrient solution in which cell cultures are cultivated. For this purpose a 5l-vessel is closed with a flange, which is provided with measuring arrangement and input and output means for a gas. In the interior of the vessel the connections for the gas are bound to the ends of a 3.5 m long polypropylene tube of porous polypropylene which is coiled into a spiral tube. The interior diameter of the polypropylene tube amounts to 5.5 mm; the wall thickness 1.5 mm. Correspondingly, the exchange surface is 0.072 m². The pore volume amounts to about 70%. The polypropylene tube is initially, over a time period of 15 minutes, soaked with ethanol, and subsequently rinsed for 2 hours with water. The maximum diameter of the pores amounts to about 0.6 $\mu$m.

The vessel is then filled with distilled water, the oxygen content of which is adjusted to 0.2 mg $O_2$/l through addition of sodium sulfite. The temperature amounts to 21° C., at which with normal pressure the corresponding saturation oxygen content amounts to 8.7 mg $O_2$/l.

The gas supply means is connected with an oxygen fish plate, whereas the gas discharge means is provided with a throttle valve. The in-feed pressure is adjusted to 1.0 bar, and the throttle valve to 0.95 bar. The liquid in the vessel is then agitated at 130 rpm with a magnetic stirrer. The oxygen content is continuously followed through use of an oxygen measuring device "Oxi 56" of the firm WTW-Weilheim.

Under these conditions, 1.4 mg $O_2$/l·h are shown to be transported through diffusion, without being able to observe the formation of any bubbles. Also after reaching the saturation limit (about 6 hours) no bubble formation occurs. There is obtained a supersaturation of the water up to 9.5 mg/l $O_2$, whereby however the periodic increase of the oxygen concentration continuously drops, whereas it remains constant up until the reaching of the saturation concentration. Above the liquid surface a fog formation is observed, from which it may be concluded that the oxygen excess is carried from the reaction medium with evaporated water.

Example 2

Following the procedure described in Example 1, constant amounts of sodium sulfite solution are admitted, which correspond to an oxygen consumption of 0.7 mg/l·h, 1.2 mg/l·h, and 1.4 mg/l·h. Through these additions the increase in oxygen correspondingly slows down or, for the 1.4 mg $O_2$/l·h equivalent amount of sodium sulfite, holds constant to the initial value. It is thus shown that one can manage to feed dosed, bubble-free oxygen into a liquid reaction medium and therewith adjust the conditions, which are of extraordinary significance for the propagation of cell cultures, namely that with a determined oxygen concentration, only so much oxygen is fed in as is consumed by the growth reaction.

It will be understood that each of the elements described above, or two or more together, may also find a useful application in other types of reactions differing from the reactions described above.

While the invention has been illustrated and described as embodied in a method for bubble-free gas feed, it is not intended to be limited to the details shown, since various modifications and structural changes may be made without departing in any way from the spirit of the present invention.

Without further analysis, the foregoing will so fully reveal the gist of the present invention that others can, by applying current knowledge, readily adapt it for varous applications without omitting features that, from the standpoint of prior art, fairly constitute essential characteristics of the generic or specific aspects of this invention.

What is claimed as new and desired to be protected by Letters Patent is set forth in the appended claims.

1. Method for the bubble-free feed of gaseous reactants of a chemical and/or biological reaction into a liquid reaction medium, comprising filling pores of a porous polymer membrane with the reaction medium and then providing one side of the porous polymer membrane with the gaseous reactants, while immersing the other side of the porous polymer membrane into the liquid reaction medium, with pressure of the gaseous reactants lying below the bubble pressure determined with the reaction medium and being at least so great that the liquid reaction medium does not pass through the porous polymer membrane to the gas side.

2. Method according to claim 1, wherein said porous polymer membrane is used in the form of a flat membrane.

3. Method according to claim 1, wherein said porous polymer membrane is used in the form of a tube.

4. Method according to claim 1, wherein said porous polymer membrane is used in the form of hollow filaments.

5. Method according to claim 1, wherein relative pore volume of the porous polymer membrane amounts to between about 50 and 90%.

6. Method according to claim 1, wherein maximum pore diameter amounts to between about 0.2 and 3 $\mu$m.

7. Method according to claim 1, wherein said porous polymer membrane is composed of regenerated cellulose, cellulose ester, polyacrylonitrile, polyamide, polyester or polyolefin.

8. Method according to claim 1, wherein said porous polymer membrane is composed of polypropylene.

* * * * *